US00PP32855P2

(12) United States Plant Patent
Karniel

(10) Patent No.: US PP32,855 P2
(45) Date of Patent: Mar. 2, 2021

(54) GRAPEVINE PLANT NAMED 'ARRATHIRTYFOUR'

(50) Latin Name: *Vitis vinifera*
Varietal Denomination: ARRATHIRTYFOUR

(71) Applicant: AGRICULTURAL RESEARCH AND DEVELOPMENT LIMITED LIABILITY COMPANY, Bakersfield, CA (US)

(72) Inventor: Shachar Karniel, Bakersfield, CA (US)

(73) Assignee: Agricultural Research and Development Limited Liability Company, Bakersfield, CA (US)

( * ) Notice: Subject to any disclaimer, the term of this patent is extended or adjusted under 35 U.S.C. 154(b) by 0 days.

(21) Appl. No.: 16/873,027

(22) Filed: Jan. 15, 2020

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205
See application file for complete search history.

*Primary Examiner* — Susan McCormick Ewoldt
(74) *Attorney, Agent, or Firm* — Lewis Roca Rothgerber Christie LLP

(57) ABSTRACT

A new distinct variety of grapevine named 'ARRATHIRTYFOUR' abundantly forms attractive meaty and crunchy seedless berries with a green skin coloration; in medium-to-large clusters which display a sweet and natural flavor. The fruit commonly is ready for harvesting during July in San Joaquin Valley of Central California, U.S.A, and displays good eating qualities as a table grape. The fruit firmness renders the fruit well amenable for handling, shipping, and storage.

1 Drawing Sheet

Classification: The present invention relates to a new *Vitis vinifera* Grapevine.

Variety denomination: The new Grapevine has a varietal denomination 'ARRATHIRTYFOUR'.

BACKGROUND OF THE INVENTION

A breeding program was initiated during the late 90's near Bakersfield in San Joaquin Valley of Central California. In 2011, during this breeding program, a new variety of *Vitis vinifera* was created by deliberate cross breeding of two parent plants by emasculation of the pollen bearing organ of the female and introducing pollen from another male origin. The female parent of the new variety was E.Z., a white fertile variety without a seed trace (non-patented in the United States).

The male parent (i.e. the pollen parent) of the new variety was GAW 15 which is a mid-season white grape variety with thin skin and a natural acid flavor (non-patented in the United States).

TABLE 1

Comparison of 'ARRATHIRTYFOUR' with its parents

| | 'ARRATHIRTYFOUR' | E.Z. | GAW 15 | Thompson Seedless |
|---|---|---|---|---|
| Pruning method | spur | cane | spur | cane |
| Bunches per vine | 42 | 32-36 | 50 | 30 |
| Berry size (mm) | 22 mm to 24 mm | 16 mm | 22 mm to 24 mm | 18 mm to 20 mm |

E.Z. X GAW 15

An artificial pollination was created, and the result was an embryo which possessed unique genetic qualities. The rudiments resulting from the above pollination were embryo rescued.

In 2012 the plant was transplanted to Bakersfield in San Joaquin Valley of Central California.

It was found that the new grapevine of the present invention possesses the following combination of characteristics:

(a) Forms attractive meaty and crunchy seedless berries with a white skin coloration; in medium-to-large clusters which display a sweet and natural flavor,
(b) Commonly bears fruit during the month of July in the San Joaquin Valley of Central California, U.S.A., and
(c) Bears fruit that is firm and is well amenable for storage, handling, and shipping.

The new variety during observation to date has displayed no visible disease, and has displayed an ability to well resist cold, drought, heat; but sensitive to direct exposure to sun and wind. The fruit of the new variety has been found to display excellent handling and shipping qualities combined with desirable dessert eating qualities.

The new variety of the present invention has been found to undergo asexual propagation beginning in 2013 near Bakersfield in the San Joaquin Valley of Central California, U.S.A. by grafting on mature Thompson rootstock (non-patented in the United States). Such asexual propagation has been conducted thereafter in successive years through 2014 and has shown that the characteristics of the new variety are strictly transmissible from one generation to another. Accordingly, the new variety undergoes asexual propagation in a true to type manner.

SUMMARY OF THE INVENTION

The new variety 'ARRATHIRTYFOUR' is a large, white seedless table grape with a high production, e.g., about 42 bunches per vine, and an average of about one to two bunches per shoot.

Asexual reproduction by micro propagation of the new variety as performed near Bakersfield, Calif., U.S.A., shows that the forgoing and other distinguishing characteristics come true to form and are established and transmitted through succeeding propagations.

BRIEF DESCRIPTION OF THE DRAWING

The accompanying photographic illustration shows typical specimens of vegetative growth of six year old specimens of the new variety, in color as nearly true as it is reasonably possible to make in a color illustration of this character. Colors in the photograph may differ from the color values cited in the detailed botanical description below, which accurately describes the colors of the new Grapevine.

FIG. 1 shows leaves, stems and grapes of 'ARRATHIRTYFOUR'.

DETAILED BOTANICAL DESCRIPTION

The chart used in the identification of colors is The R.H.S. Colour Chart of The Horticultural Society of London, Sixth Edition. The description is based on the observation of plants growing on 'Thompson Seedless' rootstock outdoors near San Joaquin Valley of Central California, U.S.A.

Vine characteristics:

*Vigor.*—Vigorous upright shoots.
*Productive capacity.*—Bearing at a natural, average capacity. Spur pruning.
*Trunk.*—Strong and developed. Diameter is 2.8" at 7" above ground. Rough with a fibrous, shaggy exterior. Light maple brown coloring (greyed orange 177 C).
*Date of bud burst in Bakersfield, Calif.*—February 26$^{th}$.

Young shoot characteristics:

*Openness of tip.*—Fully open.
*Prostrate hairs on tip.*—Sparse.
*Anthocyanin coloration of prostrate hairs on tip.*—Weak; yellow green 144B.
*Density of Erect hairs on tip.*—Medium.

Young leaf characteristics:

*Color of upper side of blade.*—Yellow green 152C.
*Color of lower surface of blade.*—Yellow green 152B.
*Prostrate hairs between main veins on lower side of blade.*—Sparse.
*Erect hairs on main veins on lower side of blade.*—Absent or very sparse.

Shoot characteristics:

*Attitude (before tying).*—Horizontal.
*Color of dorsal side of internodes.*—Yellow green 144A.
*Color of ventral side of internodes.*—Yellow green 144B.
*Color of dorsal side of nodes.*—Yellow green 144B.
*Color of ventral side of nodes.*—Yellow green 144C.
*Erect hairs on internodes.*—Absent or very sparse.
*Length of tendrils.*—4.3 inches.
*Color of tendrils.*—Yellow green 146C.
*Number of tendrils.*—6.

Flower characteristics:

*Sexual organs.*—fully developed stamens and fully developed gynoecium.
*Flower length.*—0.28 inches.
*Flower diameter.*—0.13 inches.
*Flower time of bloom.*—May 6$^{th}$.
*Pistil length.*—0.14 inches.
*Pistil color.*—Green 143A.
*Pollen color.*—Yellow 8C.
*Stamen (number).*—6.

Mature leave characteristics:

*Size of blade (inches).*—Medium (8.2"×7").
*Shape of blade.*—Wedge-shaped.
*Blistering of upper side of blade.*—Weak.
*Pattern of veins for upper blade.*—Netlike venation.
*Pattern of veins for lower blade.*—Netlike venation.
*Number of lobes.*—Five.
*Depth of upper lateral sinuses.*—Absent or very shallow.
*Arrangement of lobes of upper lateral sinuses (only varieties with lobed leaves).*—Open.
*Arrangement of lobes of petiole sinus.*—Wide open.
*Length of teeth.*—0.5 inches.
*Ratio length\width of teeth.*—Medium.
*Shape of teeth.*—Both sides convex.
*Proportion of main veins on upper side of blade with anthocyanin coloration.*—Low; Color yellow green 146C.
*Prostrate hairs between main veins on lower side of blade.*—Absent or very sparse.
*Erect hairs on main veins on lower side of blade.*—Absent or very sparse.
*Length of petiole compared to length of middle vein.*—Moderately shorter.
*Top side color.*—Green 137 C.
*Bottom side color.*—Yellow green 146 C.
*Texture.*—A little rough.
*Vein color.*—Yellow-green 146 D.
*Petiole length.*—4".
*Petiole diameter.*—0.1".
*Petiole color.*—Yellow green 146C.
*Base descriptors.*—Smooth.
*Leaf margin.*—Doubly Serrate.
*Leaf apex.*—Acute.

Reproductive organs: Stamen.

*Color.*—Green 137C.
*Size.*—0.34".
*Date of beginning of ripening in Bakersfield, Calif.*—July 15th.

Bunch characteristics:

*Bunch length (inches).*—10 inches.
*Bunch diameter (inches).*—7 inches.
*Bunch shape.*—Conic.
*Density.*—Dense.
*Color of peduncle.*—Yellow Green 144B.
*Length of peduncle of primary bunch.*—Long 2.2".
*Diameter of peduncle of primary bunch.*—0.4".
*Average bunch weight.*—3.5 lbs.

Berry characteristics:

*Size.*—very large.
*Length.*—32 mm.
*Weight.*—⅜ oz.
*Diameter.*—0.8".
*Shape.*—broad ellipsoid.
*Color of skin (without bloom).*—Yellow green 144C.

*Ease of detachment from pedicel.*—Moderately easy.
*Thickness of skin.*—Medium.
*Coloration of flesh.*—Anthocyanin absent or very weak, yellow green 150C.
*Firmness of flesh.*—Very firm.
*Particular flavor.*—None.
*Formation of seeds.*—None.
*Pedicel color.*—Yellow green 146C.
*Pedicel length.*—0.5".
*Pedicel diameter.*—0.1".
*Market use of observed plant.*—Fresh market.
*Berries per bunch.*—180.

Woody shoot characteristics:
*Woody shoot color.*—Greyed orange 166B.

Age and growing conditions: Six years growing under Y system in South Joaquin Valley (hot, dry summers).

Shipping characteristics:
*Number of days fruit has been stored under specific conditions.*—Fruit was in cold storage. Stored in poly bags inside Styrofoam boxes with sulfur pads. After 30 Days: rachises were 70% green; 2% berry shattering; no berry wrinkling or cracks were apparent.

DNA profile: To further the characterize the new ARRA variety DNA was extracted from leaf samples and DNA profiles were obtained at California Seed & Plant Lab, California USA using base pairs for 8 standard microsatellite DNA markers. The data is presented hereafter.

TABLE 2

DNA profile for 'ARRATHIRTYFOUR'

| Microsatellite DNA Marker | Allele Sizes in Base Pairs | |
|---|---|---|
| M1 | 234 | 234 |
| M2 | 239 | 249 |
| M3 | 181 | 194 |
| M4 | 204 | 210 |
| M5 | 273 | 273 |
| M6 | 135 | 145 |
| M7 | 187 | 189 |
| M8 | 251 | 255 |
| M9 | 212 | 212 |
| M10 | 237 | 247 |

The 'ARRATHIRTYFOUR' variety has not been observed under all possible environmental conditions to date. Accordingly, it is possible that the phenotypic expression may vary somewhat with changes in light intensity and duration, cultural practices, and other environmental conditions.

What is claimed:

1. A new and distinct grapevine, botanically known as *Vitis vinifera* identified as 'ARRATHIRTYFOUR'; substantially as shown and described herein.

* * * * *

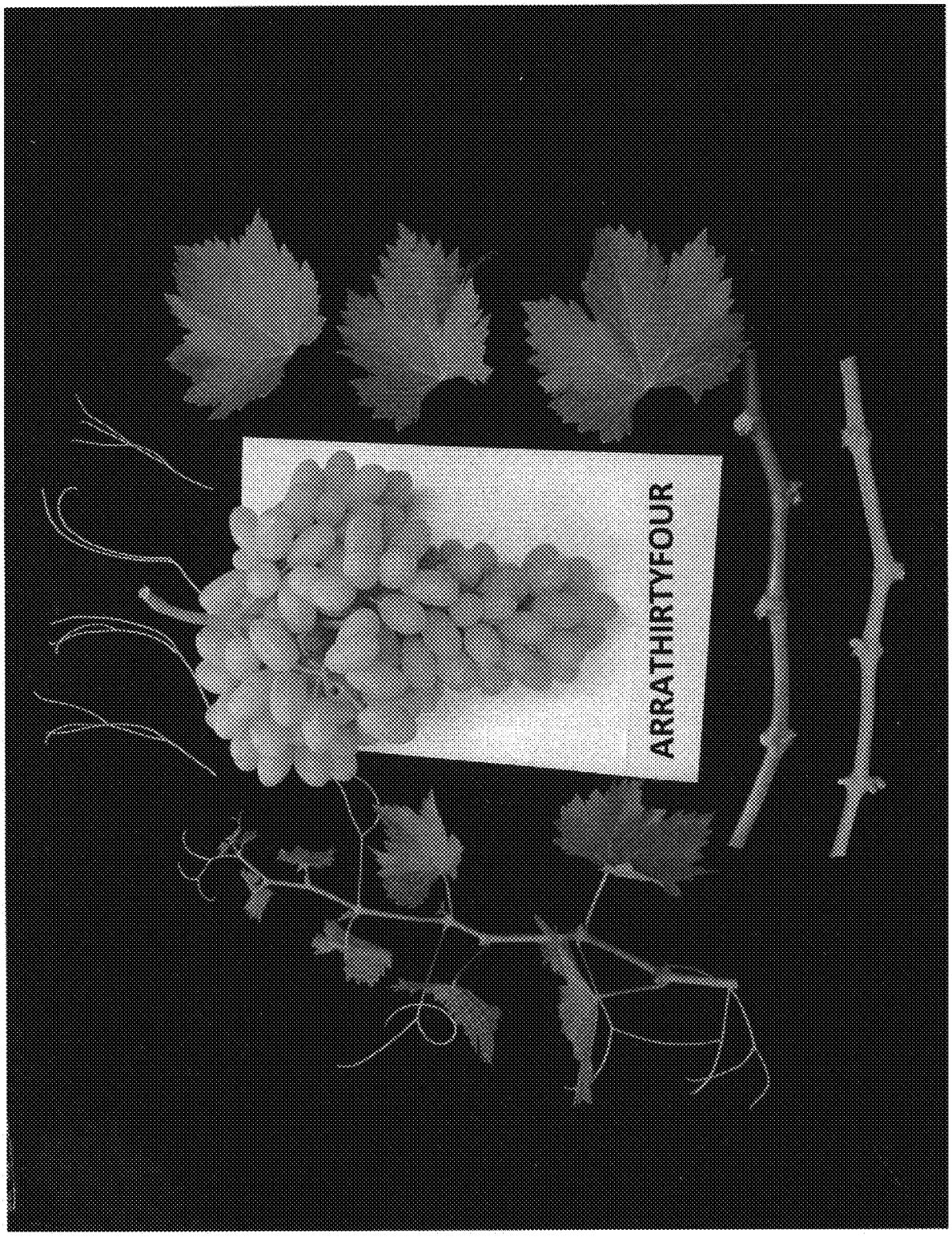
ARRATHIRTYFOUR